US006435874B1

United States Patent
Hughes

(10) Patent No.: US 6,435,874 B1
(45) Date of Patent: Aug. 20, 2002

(54) ELASTIC DENTAL DEVICE

(76) Inventor: Thomas E. Hughes, 1880 Willow Park Way, Suite A, Monument, CO (US) 80132

( * ) Notice: Subject to any disclaimer, the term of this patent is extended or adjusted under 35 U.S.C. 154(b) by 0 days.

(21) Appl. No.: 09/899,707

(22) Filed: Jul. 5, 2001

(51) Int. Cl.[7] ................................................ A61C 7/00
(52) U.S. Cl. ..................................................... 433/149
(58) Field of Search ................................ 433/148, 149, 433/15

(56) References Cited

U.S. PATENT DOCUMENTS

| 351,065 | A | * | 10/1886 | Miller |
| 368,988 | A | * | 8/1887 | Williams |
| 421,952 | A | * | 2/1890 | Marshall |
| 2,090,904 | A | * | 8/1937 | Singer |
| 2,629,930 | A | * | 3/1953 | Lane |
| 3,510,948 | A | * | 5/1970 | Walthal |
| 4,217,099 | A | * | 8/1980 | Thornton ..................... 433/148 |
| 4,259,070 | A | * | 3/1981 | Soelberg et al. ............. 433/149 |
| 5,527,181 | A |   | 6/1996 | Rawls et al. ................. 433/149 |
| 6,007,334 | A |   | 12/1999 | Suhonen ....................... 433/39 |
| 6,074,210 | A |   | 6/2000 | Garrison ....................... 433/149 |

* cited by examiner

Primary Examiner—Ralph A. Lewis
(74) Attorney, Agent, or Firm—Mayer, Brown, Rowe & Maw

(57) ABSTRACT

Structures and methods are disclosed which may be used for applying force to the base of a matrix band or cavity filling material mold during a cavity filling procedure. In a preferred exemplary embodiment of the present invention, a unitary body of elastic material is stretched preferably by applying force in opposite directions to the opposite ends of the unitary body such that a central portion of the body of material is thinned. The thinned portion of the unitary body may then be easily inserted in the space between two adjacent teeth next to the base of a matrix band or cavity filling material mold. After the unitary body has been inserted into the space between two adjacent teeth next to the base of the matrix band or cavity filling material mold, the force which has been applied to the opposite ends of the unitary body is then removed. As a result, the previously stretched elastic unitary body contracts and becomes thicker in its central portion that had been previously thinned. The contraction and thickening of the unitary body in the space between adjacent teeth fills this space and applies and outward force to the walls of this cavity. Accordingly, the contracted unitary body applies a force on the base of the matrix band or cavity filling material mold which forces the base of the matrix band or filling material mold adjacent to the base of the tooth to be filled.

11 Claims, 3 Drawing Sheets

ELASTIC DENTAL DEVICE

BACKGROUND OF THE INVENTION

1. Field of the Invention

The present invention relates generally to the field of dental tools and devices as well as the procedures for the efficient utilization of these tools. More specifically, the present invention is directed to a novel elastic dental wedge for use in cavity filling procedures which provides more uniform support for a matrix band or cavity filling material mold. The devices and methods of the present invention are both simple to use and the improved dental wedge may be quickly and easily inserted and removed.

2. Description of the Related Art

Dental wedges are conventional devices that have been around for many years in a variety of different well-known configurations. Those skilled in the art of dentistry will recognize that dental wedges are currently used in cavity filling procedures and are specifically used when cavity filling material is to be placed in the interproximal portion of a tooth. In such circumstances, it is necessary to provide additional support for the filling material when the filling material is placed on the side wall of a tooth between two adjacent teeth. In order to provide the necessary lateral support, a filling material mold that is known as a matrix band is utilized. Conventional matrix bands are essentially molds for the filling material and are typically comprised of thin curved metallic members that are placed in between two adjacent teeth. The use of the matrix band allows the filling material to conform to a desired shape while also maintaining its position relative to the cavity to be filled. Conventional dental wedges are utilized in securing and sealing the matrix band or dental filling material mold at the area of the matrix closest to the gums.

In particular, conventional dental wedges are utilized to provide support and proper placement of a matrix band or filling material mold. This allows the filling material to form to the desired contours of the side of the tooth. It is necessary to use this technique when a cavity is located between adjacent teeth and there is insufficient lateral support for the filling material.

In such situations, a thin metal support sidewall known as the matrix band is placed around the tooth requiring a filling. The matrix band is comprised of metallic thin sheet of material basically providing a sidewall that surrounds the tooth and which provides lateral support for the cavity filling material once it has been placed into the cavity. When a filling is to be made between two adjacent teeth, the matrix band is inserted around the tooth to be filled and is located between the adjacent teeth. The matrix band preferably conforms to the shape of the tooth in order to properly form the filling material.

It is well known in the field that the space or gap between two adjacent teeth at the gum line is typically not uniform in size and usually has a substantial inverted v-shape. The conventional dental wedge, as known in the art, is therefore inserted into this triangular or inverted v-shaped space in order to apply pressure at the base (gingival margin) of the matrix band. This advantageously allows the matrix band to properly conform to the natural shape of the tooth and seal the gingival margin of the cavity prior to placing the filling material into the cavity. Conventional dental wedges are usually inserted from one side of two adjacent teeth (tongue side or cheek side) and typically have a pointed configuration for ease of insertion.

For example, FIG. 1 illustrates one such conventional device and procedure of the prior art which is shown generally at 10. As shown in FIG. 1, a conventional matrix band 11 is inserted around a first tooth 12. The matrix band 11 also has a: portion that is adjacent to a second tooth 14 between the two teeth. As noted above, the use of the matrix band as a lateral support in a cavity filling procedure typically occurs when placing filling material between teeth or interproximal areas. In such a situation, the cavity to be filled is usually located such that there would be no side or lateral support or wall for the filling material without the use of the matrix band. Without the use of the matrix band, the plastic cavity filling material would not properly conform to the desired shape and could not be placed in the tooth.

One problem with the use of the matrix band 11 is that it is made of a somewhat flexible material and the outer side walls of teeth are not typically vertical and usually have a curved outward bias. Accordingly, in order to have a filling (Restoration) which matches the normal contours of the tooth, a conventional dental wedge has been historically used to in order to inwardly bias the base of the flexible metal matrix material thereby sealing this gingival margin and allowing the filling material to more accurately match the natural contours of the tooth. The con ventional dental wedge also prevents the material from being pushed beyond the gingival margin by the operator during material placement and compaction.

As shown in FIG. 1, a conventional dental wedge 16 is inserted adjacent to the metal matrix material in the gap between tooth 12 and tooth 14. The dental wedge 16 has a tapered end and a central triangular portion that is designed to substantially match the triangular space between two adjacent teeth. The tapered end of the dental wedge 16 allows the dental wedge to be easily inserted into the space between two adjacent teeth as shown.

FIG. 2 illustrates a top plan view of the matrix band surrounding the first tooth 12 with the dental wedge 16 inserted between tooth 12 and tooth 14. This is the same configuration of the elements illustrated in FIG. 1. The view shown in FIG. 2 illustrates the desired placement of the dental wedge with respect to two adjacent teeth when the dental wedge 16 has been fully inserted for the filling procedure. In particular, the tapered end of the dental wedge 16 protrudes from the side opposite the point of insertion between the two adjacent teeth 12, 14.

FIG. 3 is a side view which illustrates the details of the physical relationship between the inserted dental wedge and the matrix band when the filling material has been applied. More specifically, conventional dental wedge 16 has a substantially triangular shape at the center of the inserted portion as noted above. This triangular central portion of the dental wedge 16 is designed to match the natural triangular shape present in the gap between two adjacent teeth. As shown in FIG. 3, a matrix band 15 provides support for filling material 17, in order to properly form the filling material 17 to the natural contours of the tooth.

FIG. 4 illustrates the use of an alternate conventional matrix band structure. This view demonstrates the placement of the matrix band 11 when a dental wedge 16 is inserted between tooth 12 and tooth 14 in order to support filling material 17. The only difference between the structures illustrated in FIG. 4 and those illustrated in FIGS. 1 and 2 is that the type of matrix band is slightly different in that it does not completely surrounded the tooth 12 with the cavity to be filled. The use of the dental wedge 16 is similar in that it is intended to provide an inward bias on the base of the matrix band as shown.

FIG. 5 illustrates three alternate sizes 22, 23, 24 of the conventional dental wedges described in FIGS. 1–4. The alternate sizes for the conventional dental wedges have been utilized when filling different sized teeth. Those skilled in the art will recognize that the size of patient's teeth varies as well as the corresponding gap between two adjacent teeth. Accordingly, dental wedges of various sizes have been historically utilized in order to properly fit the various sized gaps between patient's teeth. These conventional dental wedge designs have historically been comprised of wood, plastic other some other nonelastic material and are usually designed with a tapered end in order to provide ease of insertion from either the cheek side or the tongue side.

One problem with existing conventional dental wedge designs in use today is that they are typically not very convenient for a dentist to apply. Furthermore, conventional dental wedges do not provide uniform force to the base of the matrix band structure. As a result, the use of the conventional dental wedges in fitting a matrix band to a patient's tooth does not result in the proper seal and fit for the compound contours of natural teeth that is typically desired. This is due to the non-elastic nature of most conventional dental wedge designs.

In particular, as shown in FIG. 1, due to the tapered shape of the conventional dental wedge, when the dental wedge 16 is inserted through the first side in the gap between tooth 12 and tooth 14, the force that is applied to the base of the matrix band is typically not uniform throughout the space between the two adjacent teeth 12 and 14. More force is applied to the base of the matrix band on the side of the point of insertion. Due to the physical size difference between different portions of the dental wedge, the tapered portion is unable to apply the same amount of force to the matrix band. As a result, the portions of the matrix band closest to the point of insertion for the dental wedge are typically pushed closer to the base of the tooth to be filled than those portions of the matrix band adjacent to the tapered end of the dental wedge. Accordingly, the filling material does not necessarily have the desired form fit and does not always conform to the natural contours of the patients tooth as desired.

Another shortcoming of conventional dental wedge designs is that the conventional dental wedges are physically small and can be difficult to manipulate especially when utilized by dentists having larger hands. Furthermore, the nonelastic nature of most conventional dental wedge designs makes them typically more difficult to insert.

In recognition of these and other shortcomings, several inventors have previously proposed solutions a to these problems. For example, U.S. Pat. No. 6,007,334 discloses one such proposed solution. This patent reference describes an interdental balloon for supplying force to properly bias the base of a matrix band and to allow for proper formation of the filling material. In particular, FIG. 5 of this reference shows the balloon material 11 once it is been inserted adjacent to the base of the matrix band in the space between two adjacent teeth prior to inflation. In accordance with this proposed solution, the balloon material is then inflated in order to apply force to the base of the matrix band and properly conform the filling material to the desired contours of a patient's tooth.

Although this reference describes one such proposed solution to overcoming the deficiencies and shortcomings of conventional dental wedges, this proposed solution has several problems of its own. In particular, it appears that this interdental balloon is difficult to use and is a fairly complex design. Specifically, for example, in order to use this dental wedge, it is necessary to insert a matrix band between two adjacent teeth and thereafter insert the interdental balloon material. Additionally, this proposed solution requires that the interdental balloon then be filled in order to provide the desired bias on the base of the matrix band. It appears that this proposed solution is actually more difficult to use than any of the prior art conventional dental wedge solutions.

U.S. Pat. No. 5,527,181 also discloses another proposed solution to overcoming the shortcomings and deficiencies of conventional dental wedge designs. In particular, the proposed solution set forth in this patent reference is directed to a one-piece dental wedge that is comprised of a rigid core and an elastic outer component. Both the core and the outer component are comprised of biocompatible material. This reference describes the core as being comprised of plastic, wood, metal or the like and an elastic outer component that is comprised of an elastomer of either a gel or non-gel type. The patent reference describes a tapered design which comes to a point on the end which is to be initially inserted in the space between two adjacent teeth.

Although it appears that this design may provide more uniform force to the base of the matrix band, this design also appears to have several shortcomings. In particular, due to the tapered nature of this design, the amount of force applied by the dental wedge decreases progressively from a point closest to the point of insertion toward the tapered end of the dental wedge. Additionally, this dental wedge must be physically small and therefore may be difficult to work with when it is being initially inserted into the space between two adjacent teeth.

U.S. Pat. No. 6,074,210 discloses yet another proposed solution. In particular, this dental wedge includes a generally tetrahedron shaped body having a central longitudinal apex that is flanked by a pair of resilient sidewalls. Although the resilient sidewalls of this proposed dental wedge will provide more uniform force to a matrix band than conventional dental wedge designs, it still does not overcome all of the shortcomings of the prior art because it is both physically small and is of a tapered design that is inserted between teeth from one side only. Accordingly, there still remains a need in the art to provide an improved dental wedge device that overcomes the shortcomings and deficiencies of conventional dental wedge designs.

Accordingly, one object and advantage of the present invention is to provide an improved device for supplying more uniform force to the majority of the base of a matrix band during a cavity filling procedure. Another object and advantage of the present invention is to provide an improved device for supplying more uniform force to the majority of the base of the matrix band which may be easily inserted and removed during a cavity filling procedure. Yet another object and advantage of the present invention is to provide a device which more properly form fits a matrix band to the patient's tooth contours during a cavity filling procedure. Yet another object and advantage of the present invention is to provide a device which may be inserted with a conventional dental instrument that may be easily used for inserting and removing the device that applies force to the base of a matrix band during a cavity filling procedure. Other objects and advantages of the present invention will be apparent in light of the following Summary and Detailed Description of the Presently Preferred Embodiments.

SUMMARY OF THE INVENTION

In accordance with the present invention, structures and methods are disclosed which may be used for applying more uniform force to a larger portion of a base of a matrix band or cavity filling material mold during a cavity filling procedure. In a preferred exemplary embodiment of the present invention, a unitary body of elastic material is stretched preferably by applying force in opposite directions to the opposite ends of the unitary body such that a central portion of the body of material is thinned. In accordance with the preferred exemplary embodiment of the present invention, the unitary body of elastic material is stretched with a dental dam forceps, a dental instrument which is generally known in the art. Those skilled in the art will appreciate that other tools or instruments could be used as well for stretching the unitary body of elastic material.

The thinned portion of the unitary body may then be easily inserted in the space between two adjacent teeth next to the base of a matrix band or cavity filling material mold. After the unitary body has been inserted into the space between two adjacent teeth next to the base of the matrix band or cavity filling material mold, the force which has been applied to the opposite ends of the unitary body is then removed. As a result, the previously stretched elastic unitary body contracts and becomes thicker in its central portion that had been previously thinned. The contraction and thickening of the unitary body in the space between adjacent teeth fills this space and applies and outward force to the walls of this cavity. Accordingly, the contracted unitary body applies a force on the base of the matrix band or cavity filling material mold which forces the base of the matrix band or filling material mold adjacent to the base of the tooth to be filled. In accordance with the preferred exemplary embodiment, due to the physical shape and characteristics of the unitary body of elastic material, when placed between teeth adjacent to a matrix band, a more uniform application of force to the matrix band is achieved than the force applied by prior art devices.

Once the unitary body has been expanded and the matrix band is pressed against the side of the tooth to be filled, the dentist simply performs the normal cavity filling procedure which is well known in the art. The cavity filling material conforms to the side wall of the tooth as desired due to the proper placement of the matrix band or filling material mold. The more uniform application of force which is possible through the use of the improved unitary body of elastic material provides the proper form fit of the filling material to a patients tooth.

After the filling procedure has been completed, the dentist or other person performing the procedure simply applies an outward force on the opposite ends of the unitary body of elastic material. Due to the application of this outward force, the central portion of the unitary body becomes thinner and thus may be easily removed by cutting either the tongue side or cheek side of the unitary body of elastic material when stretched. The two separate portions of the unitary body are then recovered and removed from the space between two adjacent teeth. This may be accomplished even when a matrix band or filling material mold is present. Alternatively,. the unitary body of elastic material may be removed simply by stretching thereby allowing the central portion to becomes thinner for ease of removal. The matrix band or filling material mold is then subsequently removed as in any other conventional cavity filling procedure.

In accordance with a preferred exemplary embodiment of the present invention, the unitary body of elastic material is preferably comprised of a unitary body of elastic material having two opposite ends which are preferably thicker than a central portion. In the preferred exemplary embodiment of the present invention, the elastic material of the unitary body preferably has its central portion formed to be of a substantially triangular shape. This preferred shape desirably provides a more uniform application of force in the space between two adjacent teeth. However, those skilled in the art will recognize that virtually any shape or configuration for the central portion of the unitary body may be utilized. It is only preferred that the central portion be of a substantially triangular shape in order to more properly conform to the natural shape of the space between two adjacent teeth.

In the preferred exemplary embodiment of the present invention, both opposed ends of the unitary body of elastic material preferably include holes, notches, depressions. or some other type of physical change in shape that may be easily engaged by a tool. In the preferred exemplary embodiment, the end portions of the unitary body of elastic material include holes that may be engaged by corresponding protruding members on a stretching tool. As noted above, it is preferred that the stretching tool be the conventional dental dam forceps in order to eliminate the necessity for new tools in order to perform this procedure but those skilled in the art will recognize that other tools may be utilized as well for performing the desired stretching.

In accordance with the preferred exemplary embodiment of the present invention, the holes in the unitary body of elastic material are placed over the protruding members on the stretching tool. The protruding members on the stretching tool are preferably formed of such a size to easily engage the holes in the unitary body of elastic material. The stretching tool is preferably shaped in the form of a pair of pliers wherein the protruding members are located at the end opposite to the handles. The handles are hinged such that inward application of the force on the handles produces an outward motion on the protruding members such that the unitary body of elastic material may be easily stretched.

When using the device during a cavity filling procedure, the dentist simply inserts the unitary body of elastic material on the stretching tool. Thereafter, the dentist applies the outward force on the unitary body of elastic material and inserts the material in the space between two adjacent teeth. The inward force on the handles of the stretching tool is then removed thereby allowing the unitary body of elastic material to contract into place. The conventional steps in the filling procedure and then performed and the opposite steps are then performed for removal of the elastic material.

DETAILED DESCRIPTION OF THE PRESENTLY PREFERRED EMBODIMENTS

Figure 1:
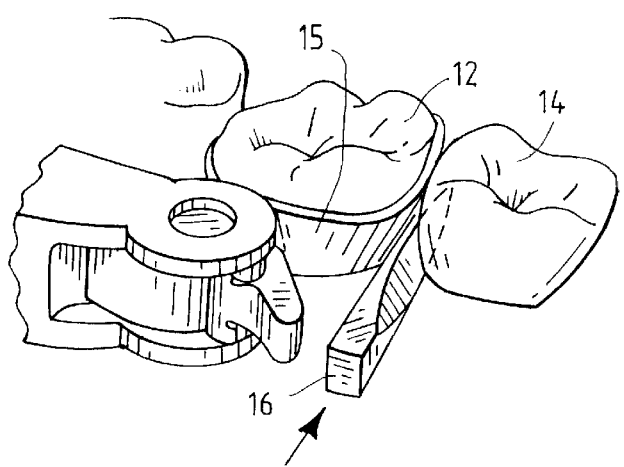
FIG. 1 illustrates a conventional cavity filling procedure using a conventional dental wedge.
Figure 5:
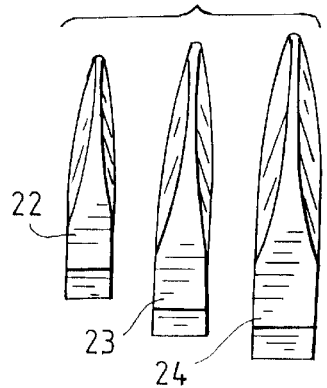
FIG. 5 illustrates three conventional dental wedge designs.
Figure 2:
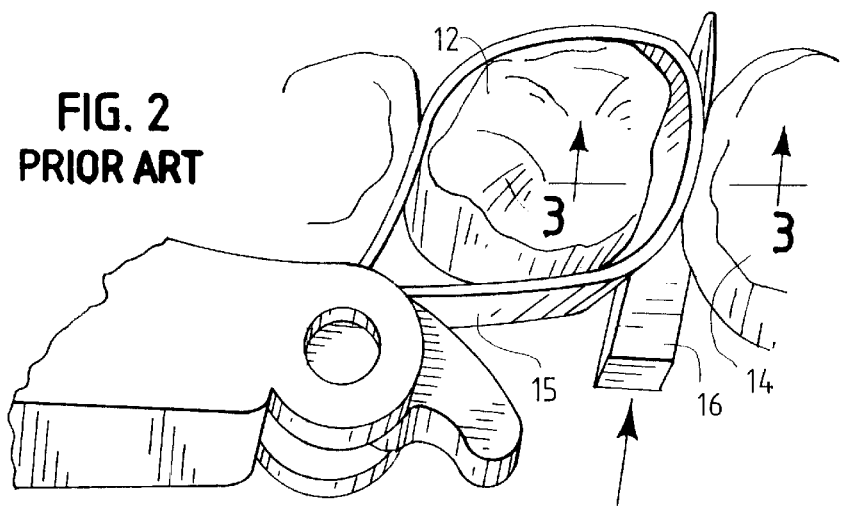
FIG. 2 illustrates an alternative view of a conventional cavity filling procedure using a conventional dental wedge.
Figure 3:
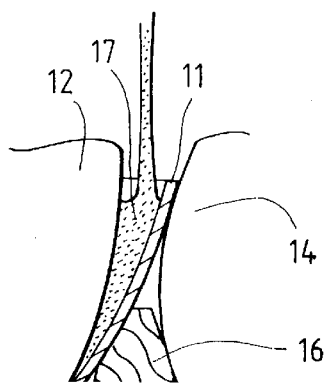
FIG. 3 illustrates an alternative view of a conventional cavity filling procedure using a conventional dental wedge.
Figure 4:
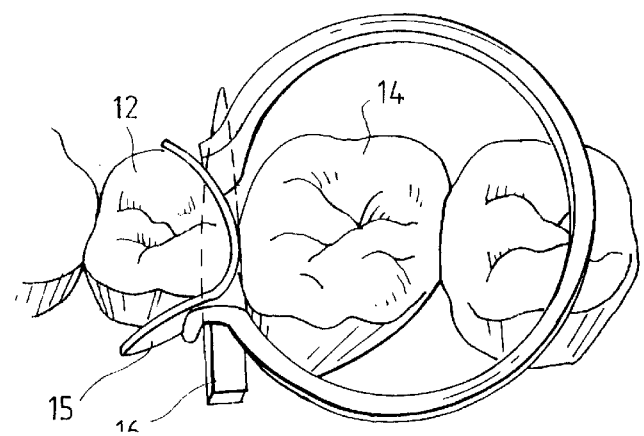
FIG. 4 illustrates an alternative view of a conventional cavity filling procedure using a conventional dental wedge.
Figure 6:
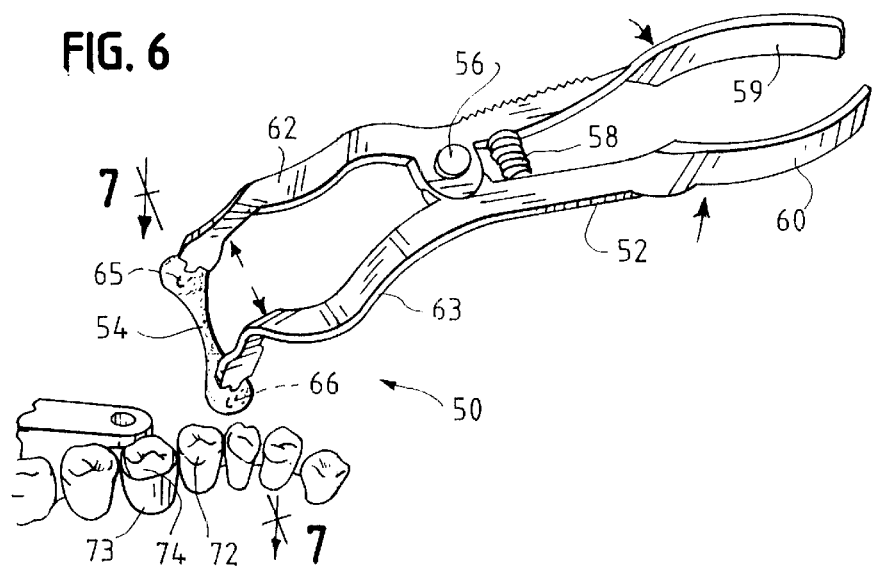
FIG. 6 illustrates a preferred exemplary embodiment of the present invention.

FIG. 6 illustrates a first preferred exemplary embodiment of the present invention which is shown generally at 10. As shown in FIG. 6, a stretching tool 52 provides a force which pulls on opposite ends of an elongated elastic member 54. As a result of the stretching of elastic member 54 the central portion of the elastic member 54 becomes much thinner. In the preferred exemplary embodiment, through application of the stretching force a central portion of the elongated elastic member 54 becomes very thin and is preferably approximately the thickness of dental floss.

Stretching tool 52 employs a central hinge 56 and a compressible spring 58. Inward force on handles 59 and 60 results in outward motion of stretching support members 62 and 63. As noted above, in the preferred exemplary embodiment, the stretching tool 52 is a conventional dental dam forceps as is known in the art. The tips of stretching support members 62 and 63 have protrusions 65, 66 for engaging corresponding holes or openings in the opposite ends of the elongated elastic member 54. As noted above, the holes in the elongated elastic member 54 may be replaced by notches, protrusions or some other physical characteristic which may be engaged by a stretching tool 52.

The separation of stretching support members 62, 63 through application of inward force on handles 59 and 60 results in stretching of the elongated elastic member 54. As a result of the stretching and the corresponding reduction in the central thickness of the elongated elastic member 54, the elongated elastic member can readily be inserted in the gap between two adjacent teeth 71, 72. As shown in FIG. 6, a matrix band 73 surrounds tooth 71. In the preferred method of inserting the elongated elastic dental wedge of the present invention, 54, the matrix band is inserted prior to insertion of the elongated elastic dental wedge as is known in the art. Once the elongated elastic dental wedge has been inserted in the desired position between adjacent teeth 71 and 72 next to the base of the matrix band 73, the inward force on handles 59 and 60 is removed thereby allowing the elongated elastic dental wedge to compress and expand in its central portion. This results in an outward force being applied in the space between adjacent teeth 71, 72 which thereby forces the base of matrix band 73 against tooth 71. This provides the desired form fit for the cavity filling material.

Figure 7:
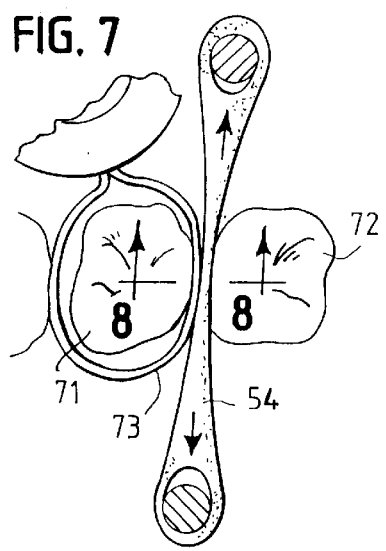
FIG. 7 illustrates an alternate view of a preferred exemplary embodiment of the present invention.

FIG. 7 is a top plan view which illustrates the stretched condition of the elastic wedge 54 during insertion of the improved dental wedge of the present invention. In particular, a first tooth 71 has a matrix band 73 surrounding the tooth 71. The matrix band 73 is also adjacent to tooth 72. As shown in FIG. 7, the improved dental wedge of the present invention is inserted into the gap between two adjacent teeth 71, 72 next to the base of the matrix band 73. It is preferred that the improved dental wedge of the present invention be stretched during insertion to preferably the thickness of dental floss. However, those skilled in the art will appreciate that it is not necessary to achieve such a thickness and other thicknesses will also work although it is simply more preferable to use a dental wedge which can achieve this thickness when stretched.

Figure 8:
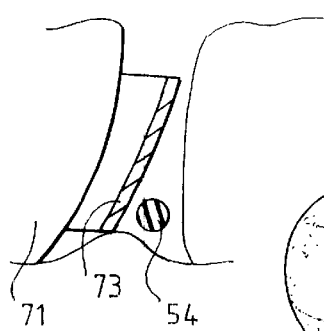
FIG. 8 illustrates an alternate view of a preferred exemplary embodiment of the present invention.

FIG. 8 is a side view which illustrates the tooth 71 and matrix band sidewall 73 with the improved elongated dental wedge of the present invention inserted in the space between two adjacent teeth. In this view the improved dental wedge is in its extended condition with its central portion thinned. This view illustrates the improved dental wedge before the stretching tool has been removed subsequent to insertion of the improved elongated elastic dental wedge of the present invention in the space between two adjacent teeth.

Figure 9:
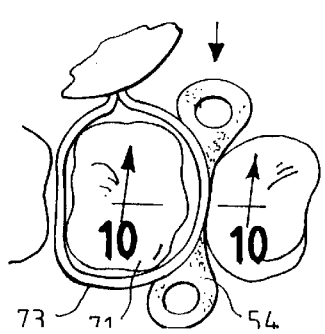
FIG. 9 illustrates an alternate view of a preferred exemplary embodiment of the present invention.

FIG. 9 illustrates a top plan view of the improved dental wedge of the present invention in its inserted state. FIG. 9 illustrates the tooth 71 and matrix band sidewall 73 with the improved elongated dental wedge of the present invention inserted in the space between two adjacent teeth. In this view the improved dental wedge is in its collapsed condition with its central portion expanded. This view illustrates the improved dental wedge after the tool has been removed subsequent to insertion of the improved elongated elastic dental wedge of the present invention in the space between two adjacent teeth.

Figure 10:
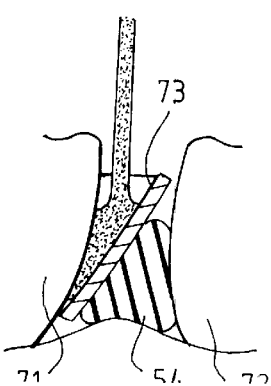
FIG. 10 illustrates an alternate view of a preferred exemplary embodiment of the present invention.

FIG. 10 Illustrates the filling material being applied to the gap between the matrix band member 73 and the tooth 71 as shown in illustration. The dental wedge preferably has a triangular or tetrahedron shape in the central portion of the collapsed form, thereby providing uniform application of force to the matrix band material when it expands in the gap between two adjacent teeth. This preferred shape provides the desired form fit for the matrix band thereby providing the preferred application of force to the matrix band.

Figure 11:
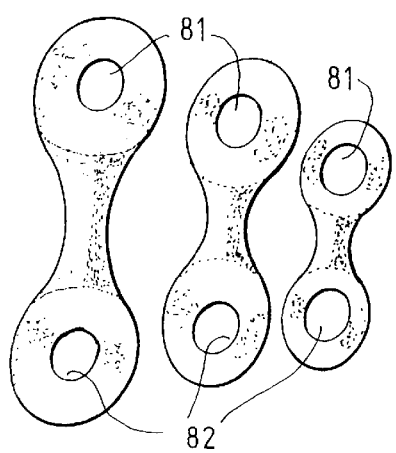
FIG. 11 illustrates three alternate sizes of the exemplary embodiment.

FIG. 11 is a top plan view which illustrates three alternate sizes for the preferred elongated elastic dental wedge of the present invention. Each of the designs of FIG. 11A, FIG. 11B, and FIG. 11C include holes 81, 82 in the opposite ends of each of the elongated elastic members. As noted above, and the preferred exemplary embodiment these holes are used by the stretching tool for engaging the ends of the elongated elastic members. FIG. 11 also illustrates the preferred shape for the elongated elastic members wherein the central portion is the thinnest point of the elongated elastic members. The portions proceeding to the ends of the elongated elastic members become increasingly thicker. This design is preferred in order to provide more uniform force around the base of the tooth. Similarly, it is preferred that the central portion of the elastic dental wedge of the present invention have a central portion which is of a triangular configuration. This ensures the desired form fit for the space between two adjacent teeth.

Those skilled in the art will recognize that it is not necessary to utilize such a shape and other configurations and designs will work for the intended purpose. Similarly, it is not necessary to include a tapered central portion. In particular, those skilled in the art will recognize that designs of uniform thickness for the unitary body of elastic material may be utilized as well. However, it is believed that improve results will be achieved by utilization of designs that conform or substantially conform to the natural contours of the shape between teeth when the unitary body is in its relaxed state. It should also be recognized that by adjusting the physical characteristics of the unitary body of elastic material, other desired effects may be achieved. Furthermore, it should be recognized that the devices and methods of the present invention may be utilized for securing other devices between teeth other than matrix bands.

Figure 12A:
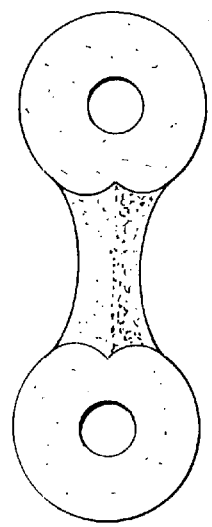
FIGS. 12A and B illustrate an alternate configuration of an exemplary embodiment of the present invention.
Figure 12B:
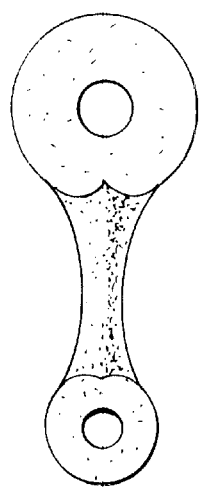

FIGS. 12A and 12B illustrate alternate configurations for the unitary body of elastic material of the present invention. In particular, FIG. 12A illustrates an embodiment wherein the body of elastic material is substantially symmetrical in shape. FIG. 12B illustrates a design wherein the body of elastic material is not substantially symmetrical. This asymmetrical design provides more of the elastic material on one side of the unitary body. This figure illustrates the fact that the unitary body of elastic material may be physically configured to apply more force on one side of the space between two adjacent teeth. These variations in the physical dimensions of the unitary body of elastic material may also be utilized to account for variations in the physical characteristics of the space between peoples teeth. Those skilled in the art will recognize that the space between teeth may not be symmetrical and accordingly asymmetrical designs may provide improve results in such circumstances.

Figure 13A:
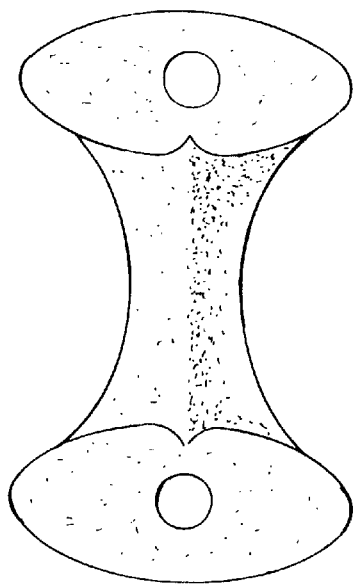
FIGS. 13A, 13B and 13C illustrate an alternate configuration of an exemplary embodiment of the present invention.
Figure 13B:
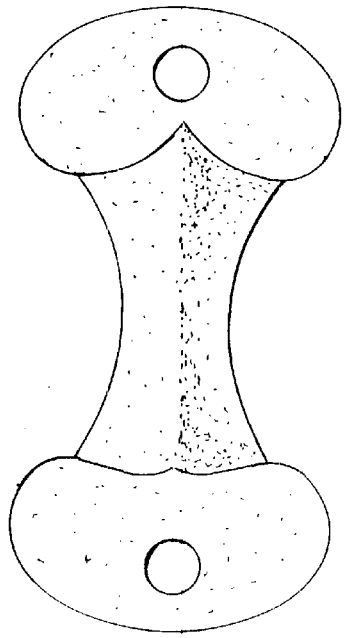
Figure 13C:
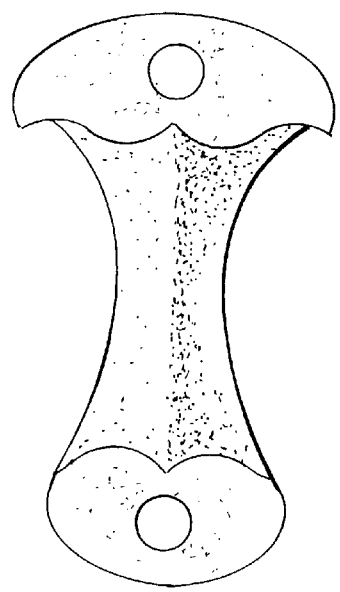

FIGS. 13A through 13C illustrate yet additional alternate configurations for the physical contours of the unitary body of elastic material. FIG. 13A illustrates a design wherein the unitary body is substantially uniform but also includes a region in the wider portions of the unitary body which curve outward away from the central region. FIG. 13B illustrates an alternate configuration wherein the unitary body includes a portion that curves outward and upward toward the opposite side of the unitary body. FIG. 13C. illustrates an asymmetrical design with an alternate configuration for the wider portions of the unitary body. Those skilled in the art will appreciate that other variations in the shape and physical configuration of the unitary body may be utilized as well.

In accordance with the preferred exemplary embodiment of the present invention, the unitary body and elastic material is comprised of an elastic polyurethane, such as, for example, medical grade pellathane. This material is currently used in the dental field for the formation of elastomeric ties or elastic literatures. It should be recognized, however, that other materials may be suitable as well. This material can be acquired from Rocky Mountain Orthodontics, Inc. of Denver Colo. Or Ortho organizers of San Marcos Calif. It is contemplated that the material will be specifically molded to the shape and physical configuration of the unitary body of elastic material. Alternatively, existing dental ligatures or other products made from this material may be trimmed or otherwise processed into the desired shape for these products.

Throughout the specification, reference has been made to the use of a unitary body of elastic material. As noted it is contemplated that essentially any elastomeric or elastic material may be utilized for the formation of the unitary body. It should be further understood that the unitary body may actually be comprised of two or more separate structures wherein the combination of the structures may be utilized to provide an elastic structure which may be stretched to be placed between a patients teeth.

I claim:

1. An elastic dental wedge comprising:
   an elongated elastic member having a first end and a second end wherein the first end and second end each define a depression capable of receiving an instrument for stretching the elastic member; and
   wherein a central portion of the elongated elastic member is thinner than a portion near the first end and a portion near the second end.

2. The elastic dental wedge of claim 1 wherein the depression in the first end and second end defines a hole in the first end and the second end of the elongated elastic member.

3. The elastic dental wedge of claim 1, wherein the central portion has a substantially triangular cross-section.

4. The elastic dental wedge of claim 2, wherein the central portion has a substantially triangular cross-section.

5. The elastic dental wedge of claim 1 wherein the depression in the first end defines a notch in the first end and the depression in the second end defines a notch in the second end of the elongated elastic member.

6. The elastic dental wedge of claim 5, wherein the central portion has a substantially triangular cross-section.

7. A method of inserting a dental wedge between-teeth comprising the steps of:
   stretching an elongated elastic member having a first end and a second end wherein the first end and second end each define a depression capable of receiving an instrument for stretching an elastic member;
   inserting the stretched elongated elastic member between two adjacent teeth.

8. The method of inserting a dental wedge between teeth of claim 7, further comprising
   a step of stretching the elongated elastic member with a stretching tool.

9. The method of inserting a dental wedge between teeth of claim 7, further comprising a step of inserting protruding members of a stretching tool into corresponding holes located on opposite ends of the elongated elastic member.

10. The method of inserting a dental wedge between teeth of claim 7, further comprising a step of providing an elongated elastic member having a central portion with a substantially triangular cross-section.

11. The method of inserting a dental wedge between teeth of claim 7 further comprising a step of providing an elongated elastic member having a notch in the first end and the second end of the elongated elastic member.

* * * * *